United States Patent [19]
Nobile et al.

[11] Patent Number: 6,098,622
[45] Date of Patent: Aug. 8, 2000

[54] AIRWAY VALVE TO FACILITATE RE-BREATHING, METHOD OF OPERATION, AND VENTILATOR CIRCUIT SO EQUIPPED

[75] Inventors: John R. Nobile; John A. Triunfo, Jr., both of Fairfield; John L. Sandor, North Haven, all of Conn.

[73] Assignee: NTC Technology Inc., Wilmington, Del.

[21] Appl. No.: 09/173,517

[22] Filed: Oct. 15, 1998

[51] Int. Cl.$^7$ ....................................................... A62B 9/00
[52] U.S. Cl. .................................. 128/205.24; 137/625.34
[58] Field of Search ........................ 128/205.24, 207.12, 128/207.16; 137/625.33, 625.34

[56] References Cited

U.S. PATENT DOCUMENTS

| | | | |
|---|---|---|---|
| 2,340,489 | 2/1944 | Pontius, III et al. | 137/153 |
| 2,486,060 | 10/1949 | Petersen | 137/625.34 |
| 2,916,047 | 12/1959 | Butcher | 137/501 |
| 3,385,320 | 5/1968 | Fahie | 137/625.34 |
| 3,435,850 | 4/1969 | Male | 137/625.34 |
| 3,556,122 | 1/1971 | Laerdal . | |
| 3,568,977 | 3/1971 | Nelson . | |
| 3,643,686 | 2/1972 | Koegel . | |
| 3,662,774 | 5/1972 | Johannisson et al. | 128/205.24 |
| 3,795,257 | 3/1974 | Fabish et al. . | |
| 3,812,878 | 5/1974 | Bird et al. . | |
| 3,859,997 | 1/1975 | Douma et al. . | |
| 3,902,516 | 9/1975 | Rudolph . | |
| 3,910,261 | 10/1975 | Ragsdale et al. . | |
| 3,933,171 | 1/1976 | Hay . | |

(List continued on next page.)

FOREIGN PATENT DOCUMENTS

WO 98/12963  4/1998  WIPO .

OTHER PUBLICATIONS

John M. Capek et al., "Noninvasive Measurement of Cardiac Output Using Partial $CO_2$ Rebreathing", IEEE Transactions on Biomedical Engineering, vol. 35, No. 9, Sep. 1988, pp. 653–661.

(List continued on next page.)

*Primary Examiner*—John G. Weiss
*Assistant Examiner*—V. Srivastava
*Attorney, Agent, or Firm*—Trask, Britt & Rossa

[57] ABSTRACT

An airway valve for re-breathing, a ventilator circuit including same and a method of operating the airway valve. The airway valve includes a housing having first and second primary passages extending through the wall thereof and mutually directly communicating within the housing through a spring-biased valve assembly in the form of first and second diaphragms respectively and simultaneously movable in tandem within the housing into and out of contact with first and second valve seats on a valve body with which the first primary passage communicates. The valve assembly also controls diversion of air flow between the first primary passage and the second primary passage into and through an enlarged volume defined by a re-breathing loop external to the housing via first and second diversion passages, which also extend through the wall of the housing. In a normal operating mode of the airway valve, a first diaphragm engages the first valve seat to preclude communication between the first primary passage and the first diversion passage, while the second diaphragm remains out of contact with the second valve seat to permit communication within the housing between the first and second primary passages and directing air flow therethrough. In a re-breathing mode of the airway valve, the second diaphragm contacts the second valve seat to preclude direct communication between the first and second primary passages, while withdrawal of the first diaphragm from the first valve seat opens communication between the first primary passage and the first diversion passage routing air flow through the re-breathing loop and back to the interior of the housing via the second diversion passage, which is in communication with the second primary passage. The diaphragms are spring-biased to the normal operating mode of the valve, and moved to the re-breathing mode by application of a differential air pressure to one of the diaphragms to overcome the spring force.

30 Claims, 10 Drawing Sheets

U.S. PATENT DOCUMENTS

| | | |
|---|---|---|
| 3,942,547 | 3/1976 | Pfitzner . |
| 3,993,059 | 11/1976 | Siostrand . |
| 4,111,228 | 9/1978 | Simionescu . |
| 4,190,045 | 2/1980 | Bartels . |
| 4,192,301 | 3/1980 | Hardwick . |
| 4,214,601 | 7/1980 | Sama . |
| 4,239,038 | 12/1980 | Holmes . |
| 4,241,756 | 12/1980 | Bennett et al. . |
| 4,267,832 | 5/1981 | Hakkinen . |
| 4,284,104 | 8/1981 | Beghini . |
| 4,333,450 | 6/1982 | Lester . |
| 4,344,456 | 8/1982 | Hostetler . |
| 4,454,893 | 6/1984 | Orchard . |
| 4,456,016 | 6/1984 | Nowacki et al. . |
| 4,462,397 | 7/1984 | Suzuki . |
| 4,463,755 | 8/1984 | Suzuki . |
| 4,493,339 | 1/1985 | Porter, Jr. . |
| 4,522,639 | 6/1985 | Ansite et al. . |
| 4,538,620 | 9/1985 | Nowacki et al. . |
| 4,543,935 | 10/1985 | Tuckey . |
| 4,606,339 | 8/1986 | Walther . |
| 4,622,964 | 11/1986 | Flynn . |
| 4,655,213 | 4/1987 | Rapoport et al. . |
| 4,699,137 | 10/1987 | Schroeder . |
| 4,712,580 | 12/1987 | Gilman et al. . |
| 4,941,476 | 7/1990 | Fisher . |
| 4,947,860 | 8/1990 | Fisher . |
| 4,986,310 | 1/1991 | Bailey et al. . |
| 5,002,050 | 3/1991 | McGinnis . |
| 5,005,568 | 4/1991 | Loescher et al. . |
| 5,020,532 | 6/1991 | Mahoney et al. . |
| 5,042,473 | 8/1991 | Lewis . |
| 5,057,214 | 10/1991 | Morris ............ 137/625.34 |
| 5,072,729 | 12/1991 | DeVries . |
| 5,103,854 | 4/1992 | Bailey et al. . |
| 5,109,840 | 5/1992 | Daleiden . |
| 5,226,449 | 7/1993 | Zimmerly . |
| 5,233,998 | 8/1993 | Chowienczyk et al. . |
| 5,255,687 | 10/1993 | McKenna . |
| 5,265,596 | 11/1993 | Sauze . |
| 5,299,579 | 4/1994 | Gedeon et al. . |
| 5,357,951 | 10/1994 | Ratner . |
| 5,438,981 | 8/1995 | Starr et al. . |
| 5,501,214 | 3/1996 | Sabo . |
| 5,503,142 | 4/1996 | Semeia . |
| 5,630,411 | 5/1997 | Holscher . |
| 5,642,726 | 7/1997 | Owens et al. . |
| 5,647,355 | 7/1997 | Starr et al. . |
| 5,678,541 | 10/1997 | Garraffa . |
| 5,746,199 | 5/1998 | Bayron et al. . |

OTHER PUBLICATIONS

John M. Capek, "Noninvasive Measurement of Cardiac Output Using Partial Carbon–Dioxide Rebreathing", UMI Dissertation Services, Dec. 1988, pp. 126–132.

Marvin A. Sackner, "Measurement of Cardiac Output by Alveolar Gas Exchange", Chapter 13: Pulmonary Capillary Blood Flow of the Handbook of Physiology—The Respiratory System IV, pp. 233–255.

M. Gama de Abreu et al., "Reliability of the Partial $CO_2$ Rebreathing Technique for Measurement of Cardiac Output", Proceedings RC IEEE–EMBS & $14^{th}$ BMESI, 1995, pp. 4.15–4.16.

Marcelo Gama de Abreu et al., "Partial Carbon Dioxide Rebreathing: A Reliable Technique for Noninvasive Measurement of Nonshunted Pulmonary Capillary Blood Flow", Crit Care Med, vol. 25, No. 4, 1997, pp. 675–683.

B. Osterlund et al., "A New Method of Using Gas Exchange Measurements for the Noninvasive Determination of Cardiac Output: Clinical Experiences in Adults Following Cardiac Surgery", Acta Anaesthesiologica Scandinavica 39, 1995, pp. 727–732.

Andras Gedeon et al., "Noninvasive Cardiac Output Determined with a New Method Based on Gas Exchange Measurements and Carbon Dioxide Rebreathing: A Study in Animals/Pigs", Journal of Clinical Monitoring, vol. 8, No. 4, Oct. 1992, pp. 267–278.

A. Gedeon et al., "A New Method for Noninvasive Bedside Determination of Pulmonary Blood Flow", Medical & Biological Engineering & Computing, Jul. 1980, pp. 411–418.

Marcelo Gama de Abreu et al., "Measurement of Pulmonary Capillary Blood Flow for Trending Mixed Venous Blood Oxygen Saturation and Oxygen Delivery", 1 page.

Marcelo Gama de Abreu et al., "Is the Partial $CO_2$ Rebreathing Technique a Useful Tool for Trending Pulmonary Capillary Blood Flow During Adjustments of Peep?", 1 page.

Tilo Winkler et al., "Pulmonary Capillary Blood Flow by Partial $CO_2$ Rebreathing: A Simulation Study Using a Bicompartmental Model of Gas Exchange", 1 page.

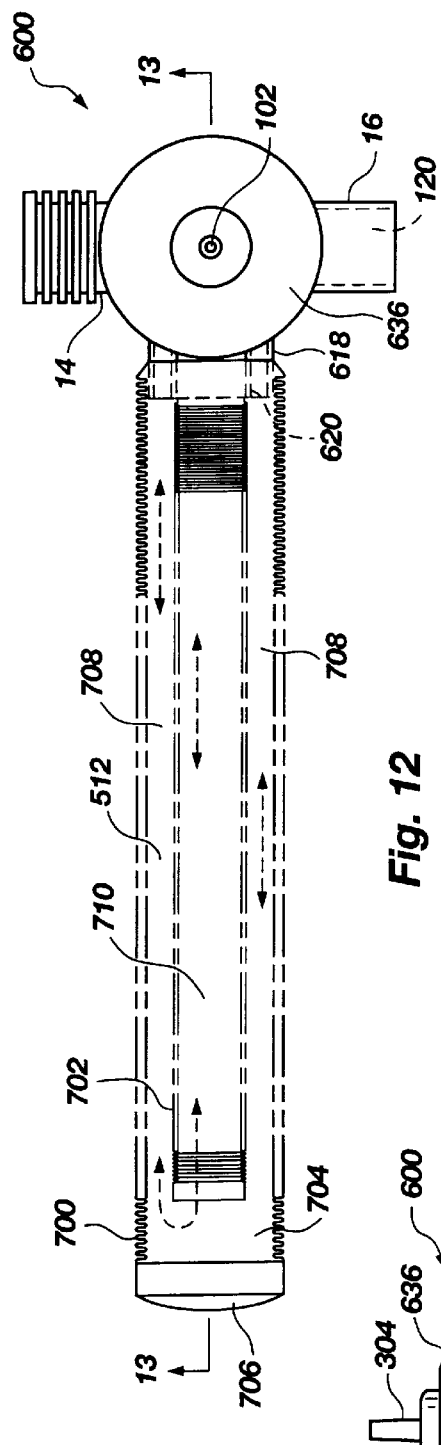
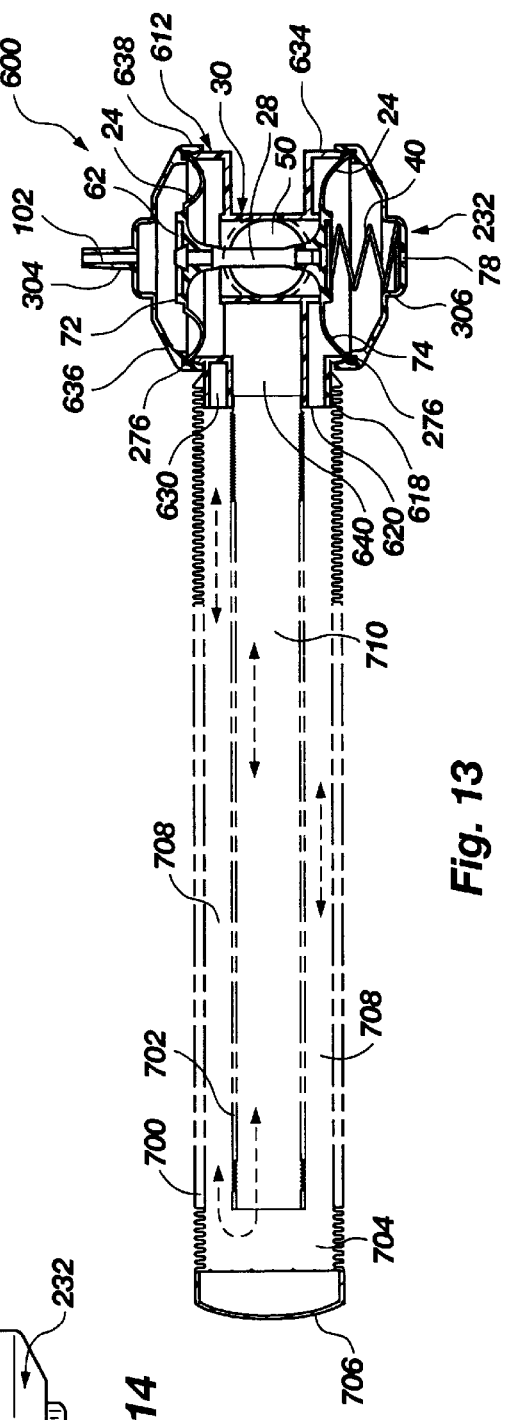
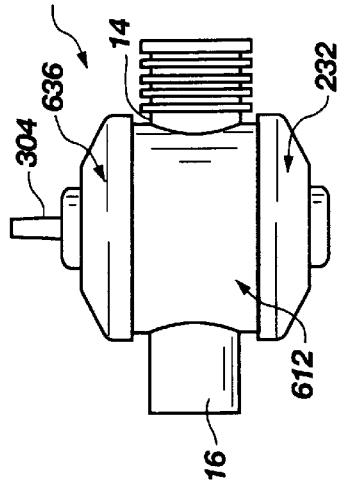
Fig. 12
Fig. 13
Fig. 14

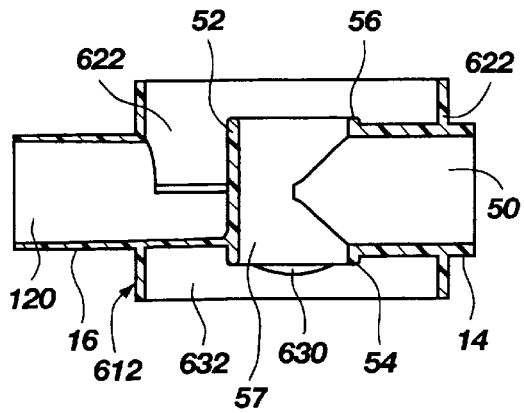
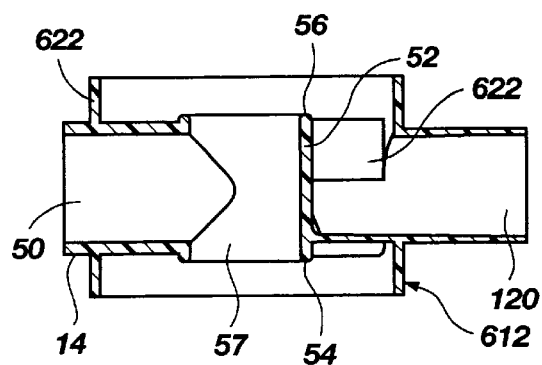
Fig. 19          Fig. 20
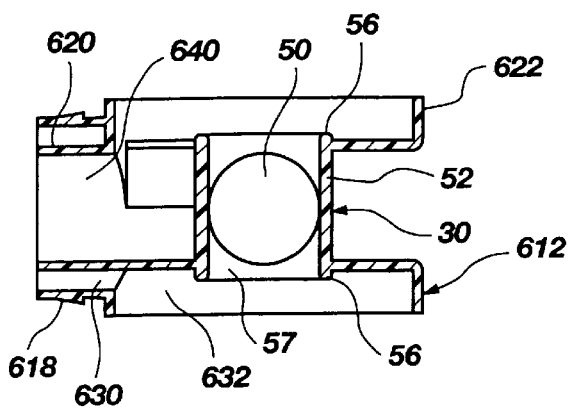
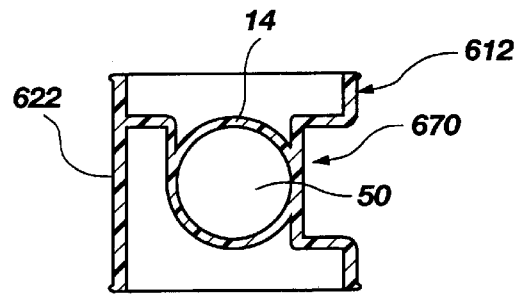
Fig. 21          Fig. 22
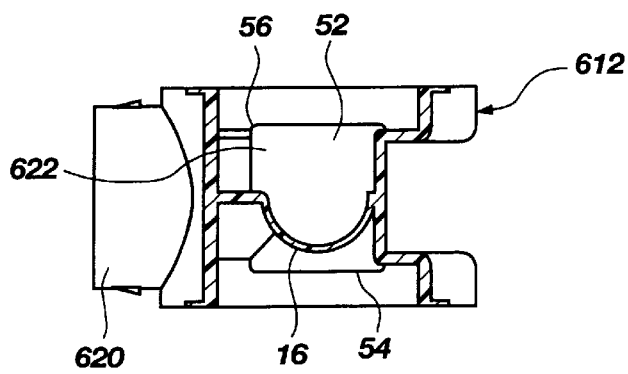
Fig. 23

AIRWAY VALVE TO FACILITATE RE-BREATHING, METHOD OF OPERATION, AND VENTILATOR CIRCUIT SO EQUIPPED

BACKGROUND OF THE INVENTION

Field of the Invention: This invention relates to non-invasive approaches for determining cardiac output in patients, specifically to partial re-breathing techniques for determining cardiac output in patients, and most particularly to airway valves for initiating and terminating extension of the respiratory path volume, as well as ventilator and other breathing circuits so equipped.

State of the Art: It is desirable, or even essential, to determine or monitor the cardiac output of a patient in many medical and surgical procedures. Invasive techniques, well known and used in the art, employ the use of catheters inserted at certain arterial points (e.g., femoral artery, jugular vein, etc.) to monitor blood temperature and pressure, in order to determine cardiac output of the patient. Although capable of producing reasonably accurate results, the invasive nature of such procedures, with the attendant trauma and risk of infection, has demonstrated an unreasonably high potential for morbidity and mortality consequences.

Adolph Fick's measurement of cardiac output, first proposed in 1870, has served as the standard by which all other means of determining cardiac output have been evaluated since that date. Fick's well-known equation, written for $CO_2$, is:

$$Q = \frac{V_{CO_2}}{(C_{v_{CO_2}} - C_{a_{CO_2}})}$$

where Q is cardiac output, $V_{CO_2}$ is the amount of $CO_2$ excreted by the lungs and $C_{a_{CO2}}$ and $C_{v_{CO2}}$ are the arterial and venous $CO_2$ concentrations, respectively. Notably, the Fick Equation presumes an invasive method (i.e., catheterization) of calculating cardiac output, because the arterial and mixed venous blood must be sampled in order to determine arterial and venous $CO_2$ concentrations.

It has previously been shown, however, that non-invasive techniques may be used for determining cardiac output while still using principles embodied in the Fick Equation. That is, expired $CO_2$ ("$pCO_2$") levels can be monitored to estimate arterial $CO_2$ concentrations and a varied form of the Fick Equation can be applied to evaluate observed changes in $pCO_2$ to estimate cardiac output. One use of the Fick Equation to determine cardiac output in non-invasive procedures requires the comparison of a "standard" ventilation event to a sudden change in ventilation which causes a change in expired $CO_2$ values and a change in excreted volume of $CO_2$. One commonly practiced means of providing a sudden change in effective ventilation is to cause the ventilated patient to re-breath a specified amount of previously exhaled air. This technique has commonly been called "re-breathing."

Prior methods of re-breathing have used the partial pressure of end-tidal $CO_2$ to approximate arterial $CO_2$ while the lungs act as a tonometer to measure venous $CO_2$. Such an approach to re-breathing has not proven to be satisfactory for determining cardiac output because the patient is required to breath directly into and from a closed volume in order to produce the necessary effect. However, it is usually impossible for sedated or unconscious patients to actively participate in inhaling and exhaling into a bag. The work of some researchers has demonstrated that the Fick Equation could be further modified to eliminate the need to directly calculate venous $P_{CO_2}(P_{VCO_2})$ by assuming that the $P_{VCO_2}$ does not change within the time period of the perturbation-an assumption that could be made by employing the partial re-breathing method. (See, Capek et al., "Noninvasive Measurement of Cardiac Output Using Partial $CO_2$ Rebreathing", *IEEE Transactions On Biomedical Engineering,* Vol. 35, No. 9, September 1988, pp. 653–661.)

Known partial re-breathing methods are advantageous over invasive measuring techniques because they 1) are non-invasive, 2) use the accepted Fick principle of calculation, 3) are easily automated, 4) require no patient cooperation and 5) allow cardiac output to be calculated from commonly monitored clinical signals. Thus, non-invasive cardiac output (NICO) techniques are rapidly gaining favor.

However, portions of known apparatus (i.e., ventilator and other breathing circuits) used for partial re-breathing techniques employed in NICO, such as airway valves for initiating and terminating an extension of a patient's respiratory path through a conduit (tubing) loop or other reservoir, are of somewhat complex, relatively expensive construction, which renders these somewhat contamination-prone and difficult to sterilize devices too expensive to be used as disposable units. In addition, conventional airway valves may unacceptably increase respiratory path volume when in normal operating (non-re-breathing) mode, may exhibit unduly high resistance to air flow in the normal operating mode, may require undesirably high energy levels to actuate, and may not return in a fail-safe manner to the normal operating mode if actuation energy is removed, and their physical configurations may render them susceptible to malfunction responsive to the presence of moisture and other contaminants typically found in an airway circuit in close proximity to the patient. Finally, conventional airway valve designs may provide, or dictate, a fixed re-breathing volume, which fixed volume may not be optimum, or even suitable, for patients of various sizes and respiratory capacities.

Thus, it would be advantageous to provide a relatively simple and inexpensive, reliable, easy to fabricate, one-use (disposable) airway valve of a design which prevents cross-contamination between patients, minimizes any significant increase in respiratory path volume or air flow resistance therethrough, when in a normal operating mode, so as to not interfere with the function of the associated breathing circuit, is usable with state-of-the art breathing circuits without modification thereto and in a manner which is easy to actuate and control with minimal modifications to existing monitors, operates in a fail-safe manner so as to default to the normal operating mode, is resistant to contaminant-induced malfunctions, and easily accommodates variation in re-breathing volumes. Furthermore, it would be desirable for such an airway valve to introduce only minimal additional equipment bulk and weight in the vicinity of the patient.

BRIEF SUMMARY OF THE INVENTION

The airway valve of the present invention provides the above-enumerated desired advantages in form and function in contrast to conventional valve designs. The airway valve includes a housing having first and second primary passages extending through the wall thereof and mutually communicating within the housing through a spring-biased valve assembly in the form of first and second diaphragms respectively, movable in tandem within the housing into and out of contact with first and second valve seats on a valve body with the interior of which the first primary passage communicates. The valve assembly also controls diversion of air flow between the first primary passage and the second primary passage into and through an enlarged volume defined by a re-breathing loop external to the housing via first and second diversion passages, which also extend through the wall of the housing. In a normal operating mode of the airway valve, a first one of the double diaphragms engages the first valve seat and thus precludes communication between the first primary passage and the first diversion passage, while the second diaphragm remains out of contact with the second valve seat, thus permitting communication within the housing between the first and second primary passages and directing air flow therethrough. In a re-breathing mode of the airway valve, the second diaphragm contacts the second valve seat, precluding communication within the housing between the first and second primary passages, while withdrawal of the first diaphragm from the first valve seat opens communication between the first primary passage and the first diversion passage, routing air flow through the re-breathing loop and back to the interior of the housing via the second diversion passage, which is in communication with the second primary passage. The diaphragms may be spring-biased to either the normal or re-breathing operating modes, although a bias toward the normal operating mode is preferred for enhanced patient safety.

Methods of airway valve operation and breathing circuits equipped with the inventive airway valve are also included within the scope of the invention.

BRIEF DESCRIPTION OF THE SEVERAL VIEWS OF THE DRAWINGS

FIG. 12 is a top elevation of another embodiment of the airway valve of the present invention, including a coaxial re-breathing loop associated with the valve;

FIG. 13 is a side sectional elevation of the valve embodiment of FIG. 12 in a normal operating mode, taken across line 13-13;

FIG. 14 is an exterior side elevation of the airway valve embodiment of FIG. 12, from the side of the valve opposite the re-breathing loop;

FIG. 19 is a side sectional elevation of the valve housing depicted in FIG. 15, taken across line 19-19;

FIG. 20 is a side sectional elevation of the valve housing depicted in FIG. 15, taken across line 20-20;

FIG. 21 is a transverse sectional elevation of the valve housing depicted in FIG. 15, taken across line 21-21;

FIG. 22 is a transverse sectional elevation of the valve housing depicted in FIG. 15, taken across line 22-22; and FIG. 23 is a transverse sectional elevation of the valve housing depicted in FIG. 15, taken across line 23-23.

DETAILED DESCRIPTION OF THE INVENTION

Referring now to FIGS. 1 through 6 of the drawings, a first embodiment 10 of the airway valve of the present invention, and its operation, will be described.

Figure 1:
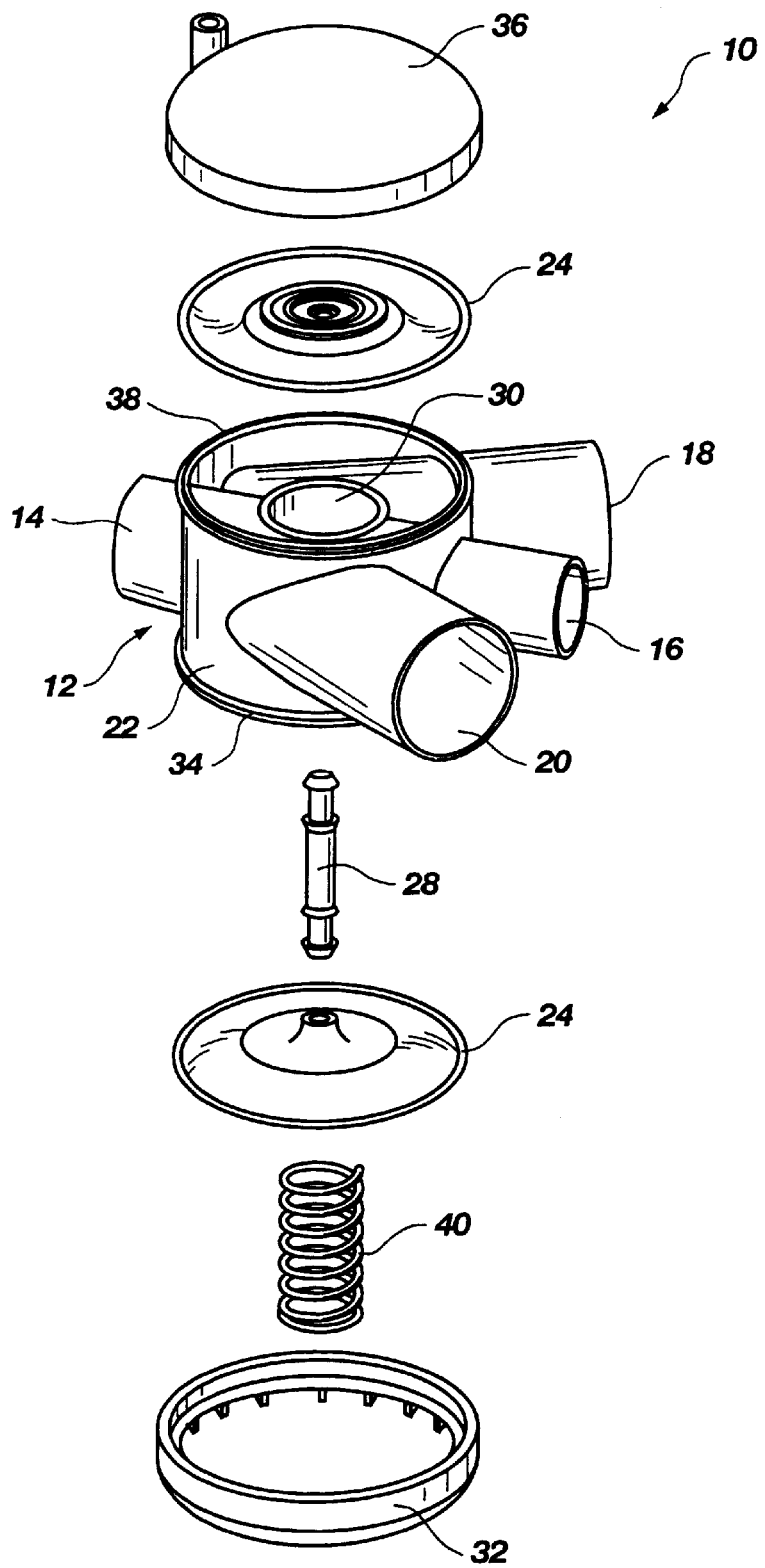
FIG. 1 is an exploded view of the component parts of a first embodiment of the airway valve of the invention.

With specific reference to FIG. 1, the component parts of airway valve 10 include a truncated cylindrical plastic housing 12 having integrally-molded tubular elements 14, 16, 18 and 20 extending through the outer wall 22 thereof Tubular elements 14 and 16 are axially aligned and oriented diametrically with respect to housing 12, while tubular elements 18 and 20 extend from housing 12 on either side of tubular element 16 and at about 30° angles thereto. First and second identical but opposingly oriented elastomeric diaphragms 24 are secured to opposite ends of shaft 28 which will extend through axially-oriented valve body 30 integrally molded as a part of housing 12. Plastic bottom cap 32 is snap-fit over the lower end 34 of housing 12, securing the outer portion of lower diaphragm 24 thereto. Similarly, plastic top cap 36 is snap-fit over the upper end 38 of housing 12, securing the outer portion of upper diaphragm 24 thereto. Coil spring 40 is compressed between the inside of bottom cap 32 and the central portion of lower diaphragm 24.

With reference to all of FIGS. 1 through 6, and most particularly to FIGS. 2, 3, 5 and 6, the detailed construction of airway valve 10 will be apparent to those of ordinary skill in the art.

Figure 2:
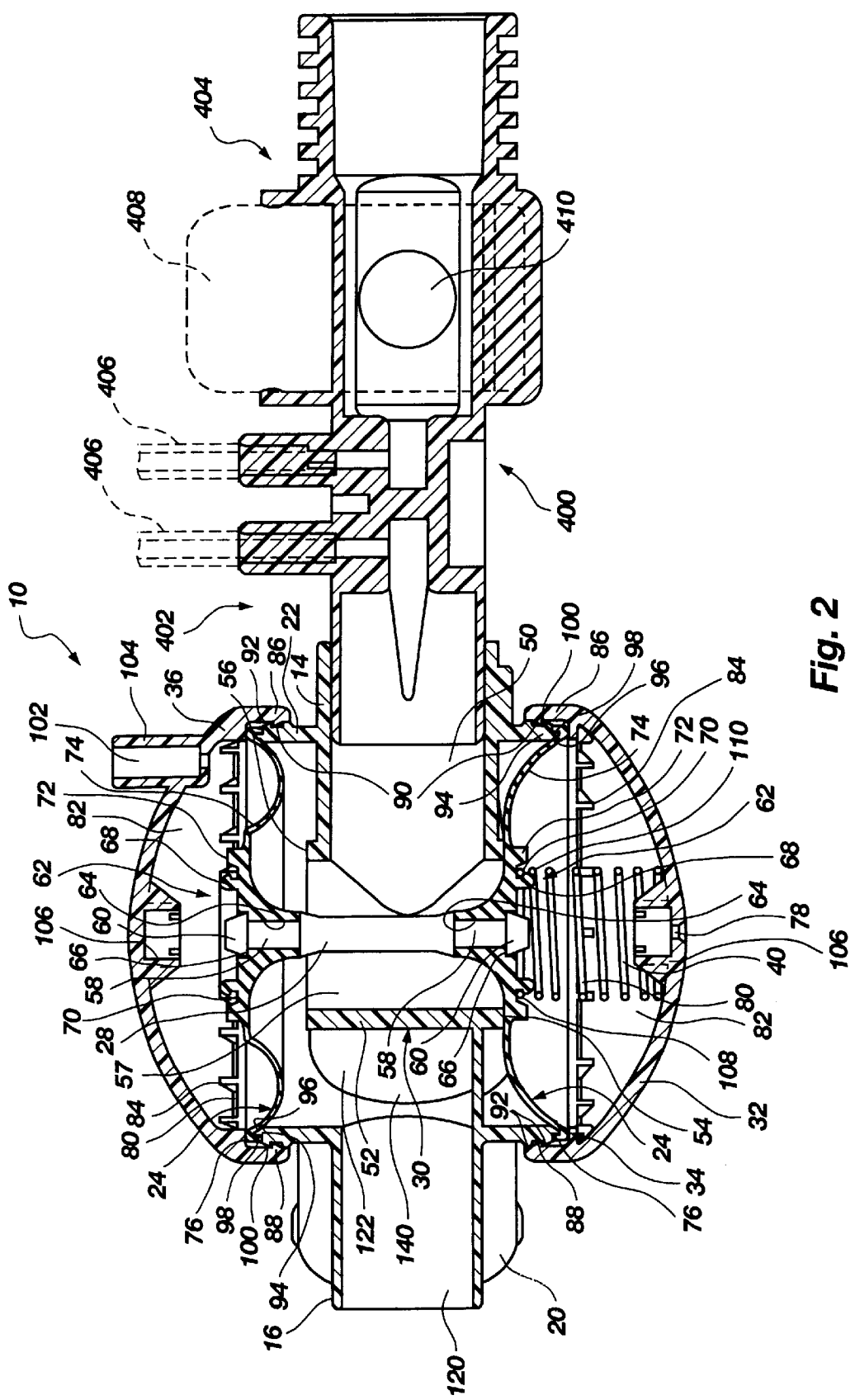
FIG. 2 is a side cross-sectional elevation of the airway valve of FIG. 1 as assembled for use and in communication with a combined flow sensor/carbon dioxide sensor as might be employed in a system according to the present invention, the airway valve being in a normal operating mode.

As shown in FIG. 2, it is contemplated that airway valve 10 will be associated in use with a combined air flow and carbon dioxide sensor 400 such as the Series 3 Pediatric/Adult Combined $CO_2$ Flow Sensor (Catalog No. 6719)

offered by Novametrix Medical Systems, Inc. of Wallingford, Conn. ("Novametrix"). The structure and operation of combined sensor 400 is disclosed in U.S. Pat. No. 5,789,660, hereby incorporated herein by this reference. The air flow sensor portion is generally designated as 402, and the carbon dioxide sensor portion as 404. Tubing 406, shown in broken lines, is employed to tap pressures within differential pressure flow sensor portion 402, while a saddle-configured, carbon dioxide sensor 408, such as the CAPNOSTAT™ $CO_2$ sensor offered by Novametrix, is disposed thereover, so as to detect carbon dioxide through windows 410 on each side of sensor portion 404. The structure and operation of the CAPNOSTAT™ sensor is disclosed in U.S. Pat. No. 5,793,044, hereby incorporated herein by this reference. Separate air flow sensors and carbon dioxide sensors may be employed in lieu of a combined sensor, and sensors functioning on other principles, as well as sensors offered by other manufacturers, may also be employed. It will be appreciated that the airway valve of the present invention has utility in any conventional or contemplated breathing circuit employing a diversion loop, and that a breathing circuit incorporating the inventive valve, as well as other components, is contemplated as encompassed by the scope of the invention.

Figure 3:
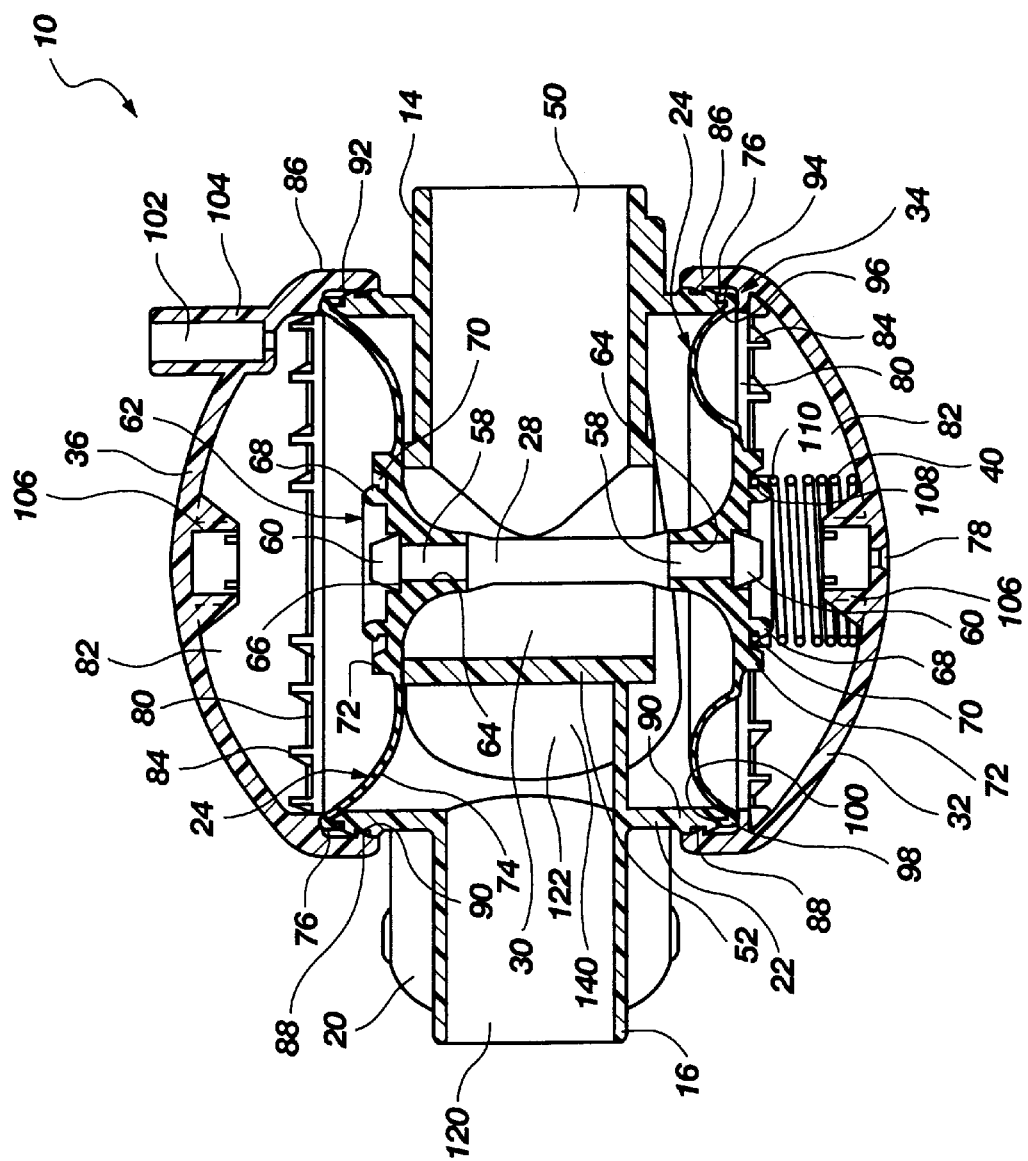
FIG. 3 is a side cross-sectional elevation of the airway valve of FIG. 1 as assembled for use and in a re-breathing mode.
Figure 4:
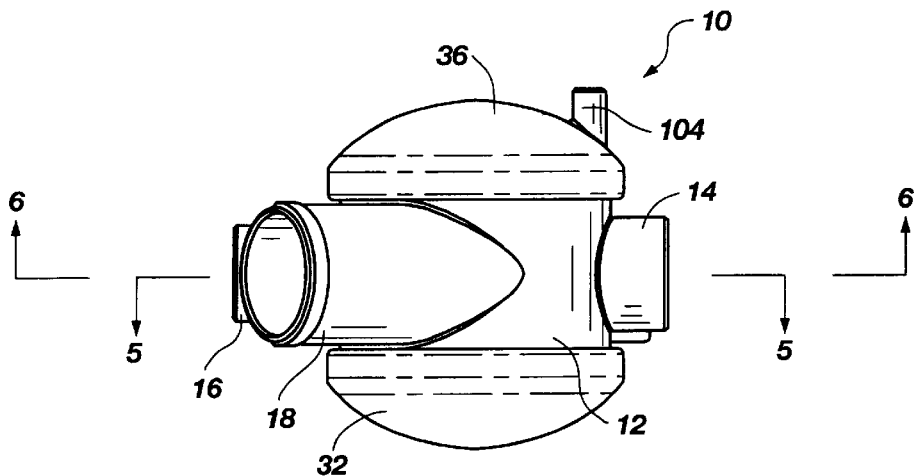
FIG. 4 is an exterior side elevation of the airway valve of FIG. 1 as assembled.
Figure 5:
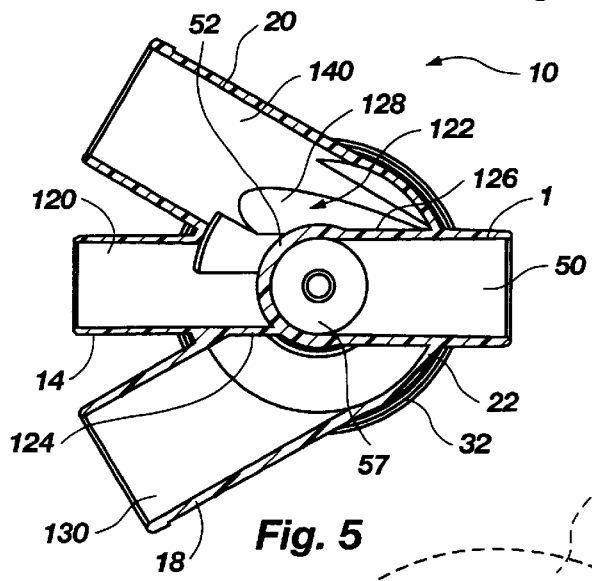
FIG. 5 is a top cross-sectional elevation through the assembled airway valve as shown in FIG. 4, taken across line 5-5, showing the air flow path through the valve in a normal operating mode.
Figure 6:
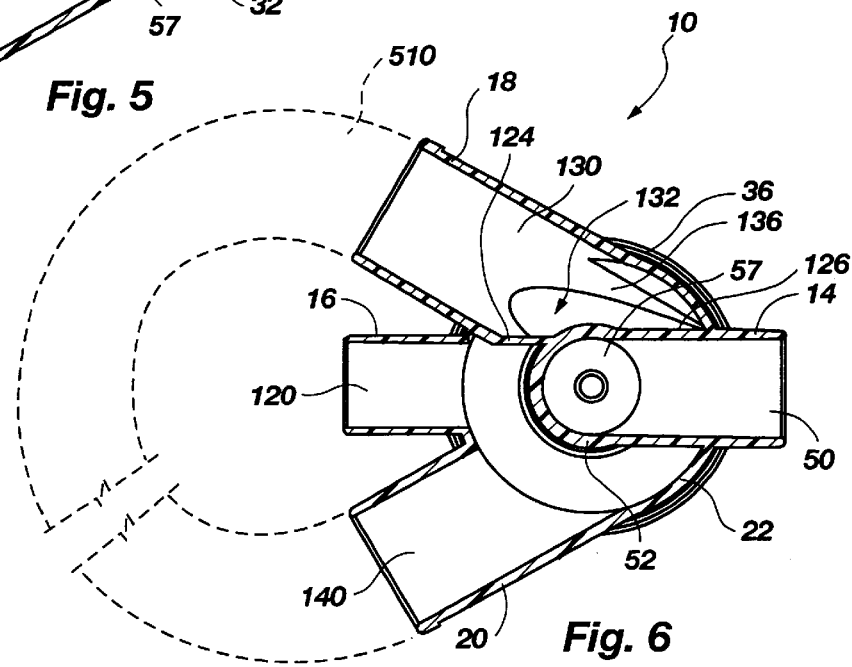
FIG. 6 is a cross-sectional elevation through the assembled airway valve as shown in FIG. 4, taken across line 6-6, showing the air flow path through the valve and an associated re-breathing loop in the re-breathing mode.
Figure 7:
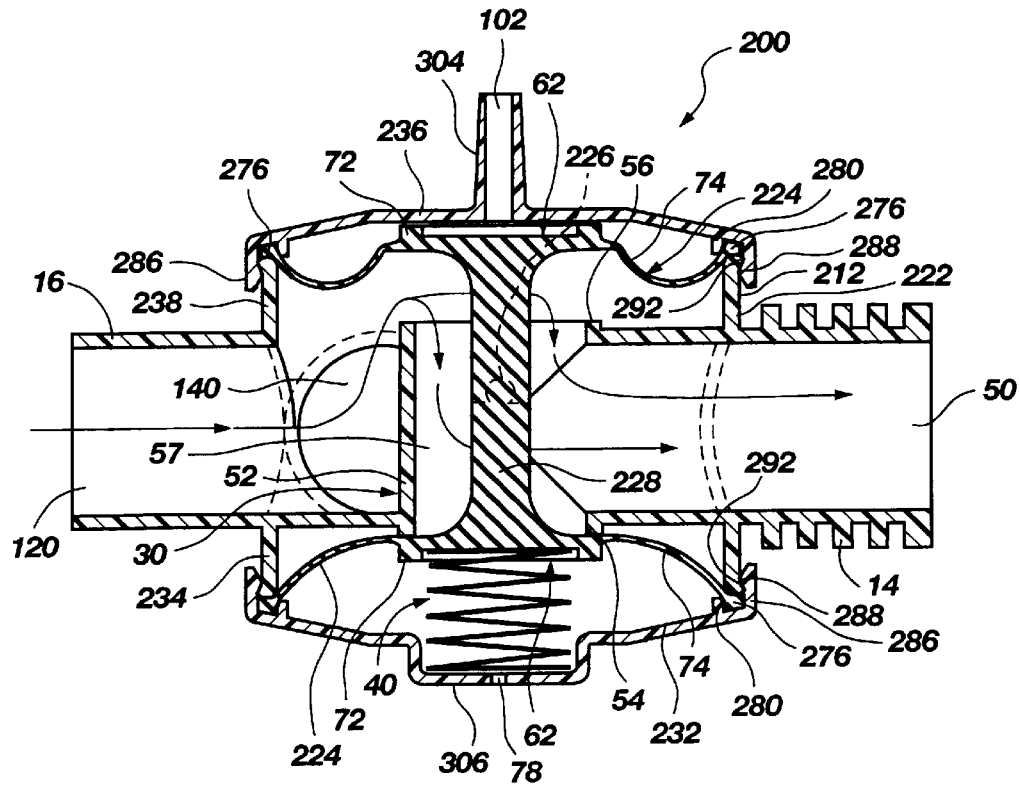
FIG. 7 is a side sectional elevation of a second embodiment of the airway valve of the invention in a normal operating mode.
Figure 8:
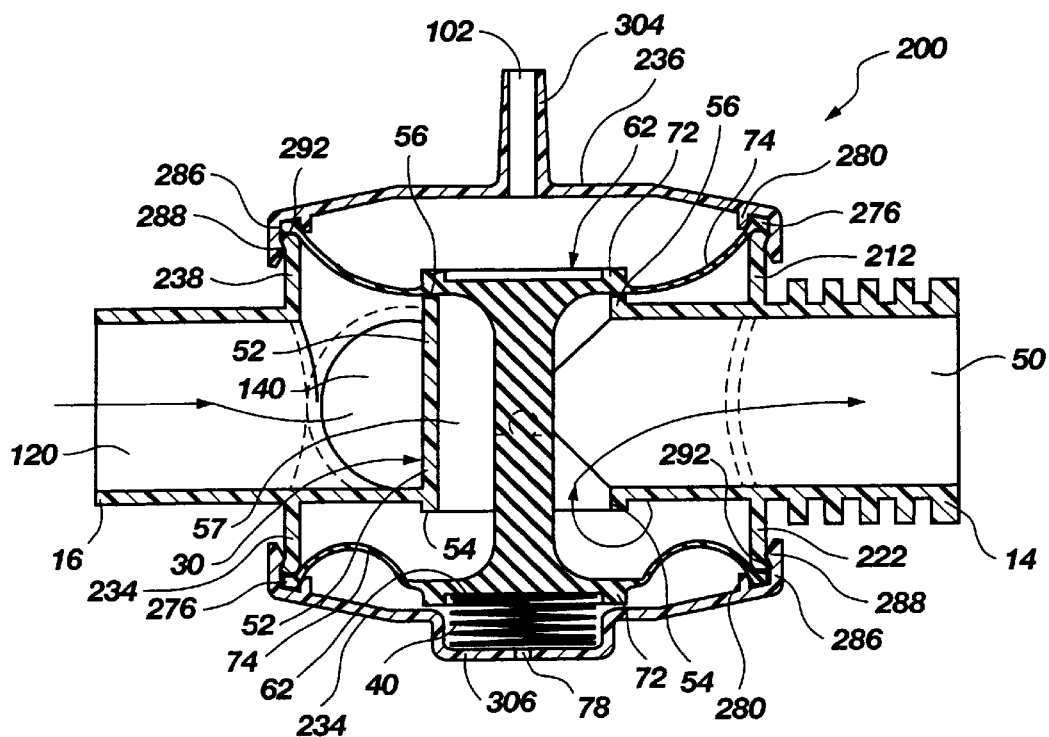
FIG. 8 is a side sectional elevation of the airway valve embodiment of FIG. 7, but in a re-breathing mode.
Figure 9:
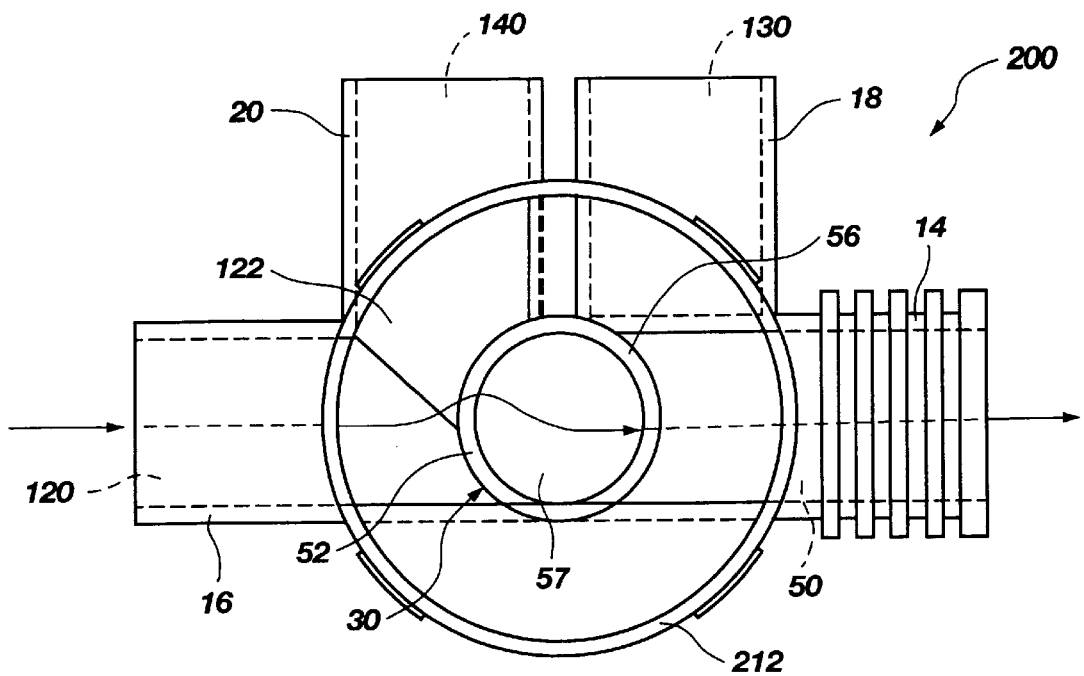
FIG. 9 is a schematic top elevation of the airway valve embodiment of FIG. 7, with the top cap removed, showing the air flow path through the valve in a normal operating mode.
Figure 10:
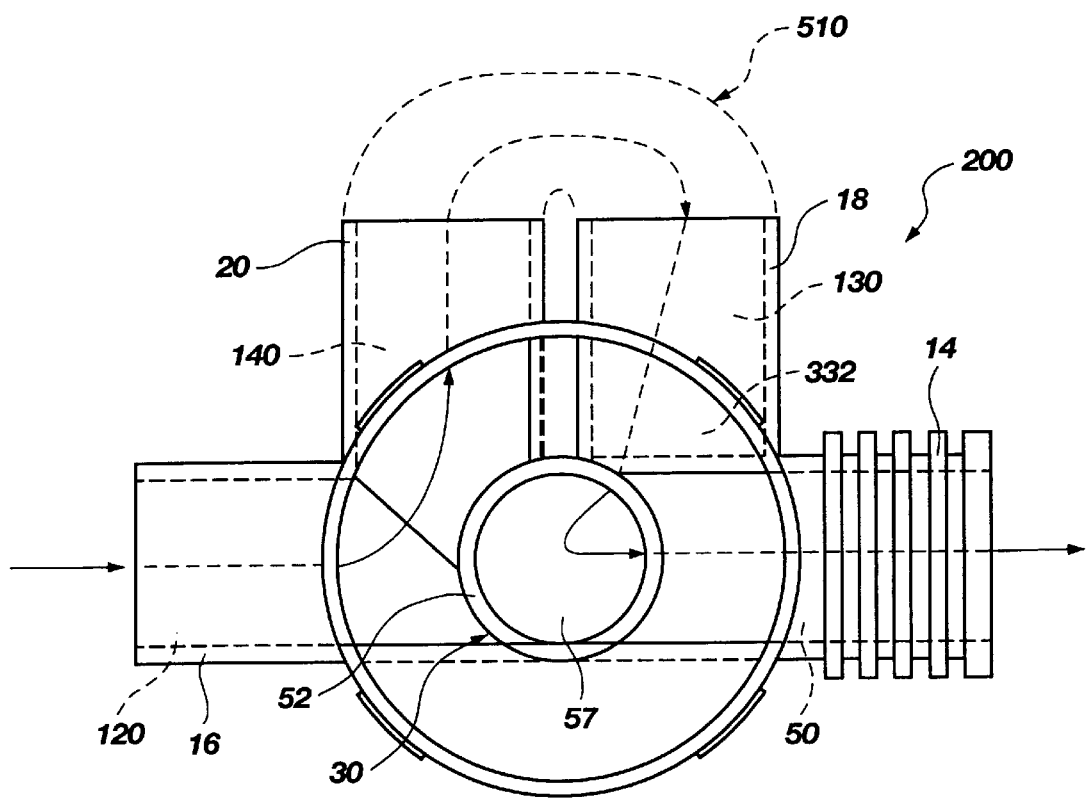
FIG. 10 is a schematic top elevation of the airway valve embodiment of FIG. 7, with the top cap removed, showing the air flow path through the valve and an associated re-breathing loop in the re-breathing mode.

Tubular element 14 extending through wall 22 of housing 12 defines first primary passage 50 and extends to and through the wall 52 of valve body 30, which is tubular, coaxial with housing 12 and includes lower valve seat 54 and upper valve seat 56 at opposing ends of bore 57. Shaft 28 is symmetrical, extends through valve body 30, and includes portions of reduced diameter 58 at each end, surmounted by frustoconical tips 60. Diaphragms 24, which are circular and identical in size and configuration, each include a central seat contact portion 62 having a central aperture 64 therethrough with an enlarged diameter entry bore 66. The distance between the floor of entry bore 66 and the opposing end of central aperture 64 is substantially the same as the length of reduced diameter portions 58 on shaft 28, and the diameter of central aperture 64 is of substantially the same diameter as (preferably slightly smaller than) that of reduced diameter portions 58. Radially outboard of entry bore 66 lies annular spring retention flange 68, the outer circumference of which lies over an annular spring retention recess 70, and outboard of annular spring retention recess 70, an enlarged thickness annular seat contact rim 72 lies at the outer periphery of central seat contact portion 62. A thin, annular, flexible skirt portion 74 extends from rim 72 to the outer periphery of each diaphragm 24, at which is located annular shoulder 76. As can be seen in FIGS. 2 and 3, diaphragms 24 are opposed in orientation on either side of valve body 30 and are connected by shaft 28 extending through valve bore 57, each of the diaphragms 24 being sealingly secured to shaft 28 at a reduced diameter portion 58 after a tip 60 of the shaft 28 is inserted through a central aperture 64 to expand same, and the elastomeric material of the diaphragm subsequently contracts over a reduced diameter portion 58.

Lower diaphragm 24 is clamped to the lower end 34 of housing 12 by bottom cap 32, which is convex, or dome-shaped, and includes air vent 78 at the center thereof. Annular diaphragm retention flange 80 extends inwardly from the interior wall 82 of bottom cap 32, and is braced against deflection by a plurality of ribs 84 extending between annular diaphragm retention flange 80 and the interior wall 82. Radially outboard of annular diaphragm retention flange 80 and extending axially inwardly as bottom cap 32 is mounted to housing 12, annular wall 86 includes a radially-inwardly extending annular locking protrusion 88 which, when bottom cap 32 is placed over the lower end 34 of housing 12, engages annular locking recess 90, defined between radially outwardly-extending shoulders 92 on the outer surface of the housing 12. Lower end 34 of housing 12 also includes an annular protrusion 94 at the outermost tip thereof having a frustoconical inner surface 96 and an axially-extending outer surface 98 from which a radially-oriented annular surface 100 extends. Shoulder 76 of diaphragm 24 lies peripherally outward of protrusion 94, and shoulder 76 and flexible skirt portion 74 are compressed and sealingly clamped against protrusion 94 by diaphragm retention flange 80. Bottom cap 32 (as well as top cap 36) includes an axially-located, hollow, substantially cylindrical protrusion 106 having wedge-shaped bracing ribs exterior thereto on the interior wall 82, air vent 78 opening into the cavity in the center of protrusion 106, and thereby being protected during operation from clogging by moisture and other patient-generated contaminants collecting in bottom cap 32. Protrusion 106, with its wedge-shaped exterior ribs, is operative in bottom cap 32 to constrain coil spring 40 against lateral movement. The axially inner end of coil spring 40, and specifically at least a portion of the first loop 108, is retained in annular spring retention recess 70 of lower diaphragm 24, with annular spring retention flange 68 thereof protruding at least partially between the first loop 108 and the second loop 110.

Upper diaphragm 24 is similarly clamped to the upper end 38 of housing 12 by top cap 36, the upper end 38 of housing 12 being configured substantially the same as lower end 34, top cap 36 being configured for engagement with upper end 38 and with upper diaphragm 24, as previously described, with respect to bottom cap 32 and lower diaphragm 24. Top cap 36 is substantially identical to bottom cap 32, but does not include an air vent 78. Instead, a pressure port 102 defined by tubular protrusion 104 near the outer periphery of the top cap 36 provides actuation energy for airway valve 10 from an external positive pressure source (not shown).

Tubular element 16 extending through wall 22 of housing 12 defines second primary passage 120, but terminates short of valve body 30, selectively communicating with first primary passage 50 through open-topped semi-annular cavity 122 and valve bore 57 when upper valve seat 56 is not occluded by upper diaphragm 24. Semi-annular cavity 122 is substantially defined between the wall 22 of housing 12 and wall 124 of first diversion passage 130, valve bore wall 52 and wall 126 of first primary passage 50, and includes a floor 128 extending between housing wall 22 and first diversion passage wall 124, valve bore wall 52 and first primary passage wall 126 (see especially FIG. 5). As may best be seen in FIGS. 2 and 3, upper valve seat 56 extends slightly above first primary passage 50 and second primary passage 120.

Tubular element 18 extends through wall 22 of housing 12 and defines first diversion passage 130, which selectively communicates with first primary passage 50 through open-bottomed semi-annular cavity 132 and valve bore 57 when lower valve seat 54 is not occluded by lower diaphragm 24. Semi-annular cavity 132 is substantially defined between the wall 22 of housing 12 and wall 124 of first diversion passage 130, valve bore wall 52 and first primary passage wall 126, and includes a ceiling 136 extending between housing wall 22 and first diversion passage wall 124, valve bore wall 52 and first primary passage wall 126 (see especially FIG. 6). As may best be seen in FIGS. 2 and 3, lower valve seat 56 extends slightly below first primary passage 50 and second primary passage 120.

Tubular element 20 extending through wall 22 of housing 12 defines second diversion passage 140, which communicates with second primary passage 120 through semi-annular cavity 122. First diversion passage 130 and second diversion passage 140 communicate exterior to airway valve 10 through a tubing loop 510 (see FIG. 11), but do not communicate within housing 12.

In operation, airway valve 10 is cycled between a normal operating mode (FIG. 2) and a re-breathing mode (FIG. 3) by application or release of a positive pressure (i.e., greater than ambient) through pressure port 102. In the normal operating mode of airway valve 10, which is maintained in the absence of the aforementioned positive pressure, coil spring 40 pushes lower diaphragm 24 upwardly against lower valve seat 54, precluding communication within housing 12 between first primary passage 50 and first diversion passage 130. Since upper diaphragm 24 is linked to lower diaphragm 24 through shaft 28, this position elevates upper diaphragm 24 above and out of contact with upper valve seat 56, opening communication through the open top of semi-annular cavity 122 between first primary passage 50 and second primary passage 120. Upon application of sufficient positive pressure to the closed chamber defined between upper diaphragm 24 and the interior of top cap 36, on the order of (by way of example only) about 2.5 psi (17 kPa), the spring force (again, by way of example only) of about 0.5 pound (2.3 Newtons) of coil spring 40 against lower diaphragm 24 may be overcome and upper diaphragm 24 pushed axially downward against upper valve seat 56 to preclude the communication within housing 12 between first primary passage 50 and second primary passage 120. Simultaneously, shaft 28 transmits the movement of upper diaphragm 24 to lower diaphragm 24, pushing the latter away from lower valve seat 54 and opening communication between first primary passage 50 and first diversion passage 130 through the open bottom of semi-annular cavity 132. Air vent 78 in bottom cap 32 prevents trapping of air pressure between lower diaphragm 24 and bottom cap 32, which pressure might otherwise impair operation of airway valve 10. In the re-breathing mode of airway valve 10, an extended airway path (and its attendant increased system volume) is opened between first primary passage 50 and second primary passage 120 through the re-breathing loop 510 interconnecting first diversion passage 130 and second diversion passage 140. While second diversion passage 140 is always in communication with second primary passage 120 through semi-annular cavity 122, substantially no air will flow therebetween when lower valve seat 54 is occluded because the path between first diversion passage 130 and first primary passage 50 is closed.

Referring now to FIGS. 7 through 10 of the drawings, another embodiment 200 of the airway valve of the present invention will be described. Airway valve 200 is similar in some respects to airway valve 10 and like components are identified by like reference numerals for clarity. Four tubular elements 14, 16, 18 and 20 extend from plastic housing 212, formed as a truncated cylinder. Tubular elements 14 and 16 are axially aligned and diametrically oriented with respect to housing 212, while tubular elements 18 and 20 extend transversely to elements 14 and 16 and off to one side of housing 212. Coaxial valve body 30 resides within housing 212, and tubular element 14 extending through the wall 222 thereof defines a first primary passage 50 communicating with valve body bore 57 through the wall 52 of valve body 30, at opposing ends of which are located lower valve seat 54 and upper valve seat 56. In lieu of the discrete diaphragms employed in airway valve 10, a unitary shaft and double diaphragm structure is employed, including diaphragm elements 224 at each end thereof, connected by an intermediate shaft portion 228. One of the diaphragm elements 224 is pulled through valve body bore 57 to assemble the double diaphragm structure with housing 212. Alternatively, as shown by broken lines 226, the structure may be formed as two components and snap-fit and/or bonded together.

Each diaphragm element 224 includes a central valve seat contact portion 62, having an enlarged thickness annular seat contact rim 72 at the outer periphery thereof. A thin, annular, flexible skirt portion 74 extends from rim 72 to the outer periphery of each diaphragm element 224, at which is located an annular shoulder 276.

Lower diaphragm element 224 is clamped to the lower end 234 of housing 212 by bottom cap 232, which is convex, or dome-shaped, and includes an air vent 78 at the center thereof at the bottom of spring retention cavity 306. The outer periphery of bottom cap 232 includes an annular, axially-oriented diaphragm retention shoulder 280 near annular wall 286, which includes a radially inwardly-facing annular locking protrusion 288, which snaps over a radially outwardly-extending shoulder 292 on the outer surface of housing 212 to trap and compress annular shoulder 276 of lower diaphragm element 224 between bottom cap diaphragm retention shoulder 280, annular wall 286 and the lower end 234 of housing 212. A coil spring 40 is interposed between bottom cap 232 and lower diaphragm element 224, lateral movement of coil spring 40 being prevented by disposition of its lower end in spring retention cavity 306 and its upper end within rim 72.

Upper diaphragm element 224 is similarly clamped between top cap 236 and upper end 238 of housing 212, top cap 236 and the upper end 238 of housing 212 being configured substantially the same as bottom cap 232 and loser end 234 of housing 212 for mutual engagement by snap-fit with annular shoulder 276 of upper diaphragm element 224 therebetween. Top cap 236 is similar to bottom cap 232, but omits a spring retention cavity and includes a pressure port 102, defined by tubular protrusion 304, at the center of top cap 236.

Tubular element 16 extending through wall 222 of housing 212 defines second primary passage 120, but terminates short of valve body 30, selectively communicating with first primary passage 50 through semi-annular cavity 122 and valve bore 57 when upper valve seat 56 is not occluded by upper diaphragm element 224.

Tubular element 18 extending through wall 222 of housing 212 defines first diversion passage 130, which selectively communicates with first primary passage 50 through semi-annular cavity 332 and valve bore 57 when lower valve seat 54 is not occluded by lower diaphragm element 224.

Tubular element 20 extending through wall 222 of housing 212 defines second diversion passage 140, which communicates with second primary passage 120 through semi-annular cavity 122. First diversion passage 130 and second diversion passage 140 communicate exterior to airway valve 10 through a tubing loop 510 (see also FIG. 11), but do not communicate within housing 212.

In operation, valve 200 is cycled between a normal operating mode (FIGS. 7 and 9) and a re-breathing mode (FIGS. 8 and 10) by application or release of a positive pressure (i.e., greater than ambient) through pressure port 102. As with airway valve 10, airway valve 200 is spring-biased to the normal operating mode. In this mode, lower diaphragm element 224 is pushed toward lower valve seat 54 by coil spring 40, and communication between first primary passage 50 and first diversion passage 130 is precluded. Upper diaphragm element 224, which is linked to lower diaphragm element 224 through intermediate shaft portion 228, is pushed upwardly away from upper valve seat 56, permitting communication between first primary passage 50 and second primary passage 120 through open semi-annular cavity 122 and valve bore 57. Upon application of sufficient positive pressure to the closed chamber defined between upper diaphragm element 224 and the interior of top cap 236, the force of coil spring 40 is overcome and upper diaphragm element 224 is pushed axially downward toward upper valve seat 56 to preclude direct communication within housing 212 between first primary passage 50 and second primary passage 120 in airway valve 200's re-breathing mode. As upper diaphragm element 224 is pressed against upper valve seat 56, intermediate shaft portion 228 transmits the motion of upper diaphragm element 224 to lower diaphragm element 224, moving same away from lower valve seat 54. Air vent 78 prevents trapping of pressure between lower diaphragm element 224 and bottom cap 232, which might otherwise impair operation of airway valve 200. Communication between first primary passage 50 and first diversion passage 130 is thus opened, and an extended airway path (and its attendant increased system volume) is opened between first primary passage 50 and second primary passage 120 through the re-breathing loop 510 defining dead-space 512 interconnecting first diversion passage 130 and second diversion passage 140. While second diversion passage 140 is always in communication with second primary passage 120, substantially no air will flow therebetween when lower valve seat 54 is occluded because the path between first diversion passage 130 and first primary passage 50 is closed.

Figure 11:
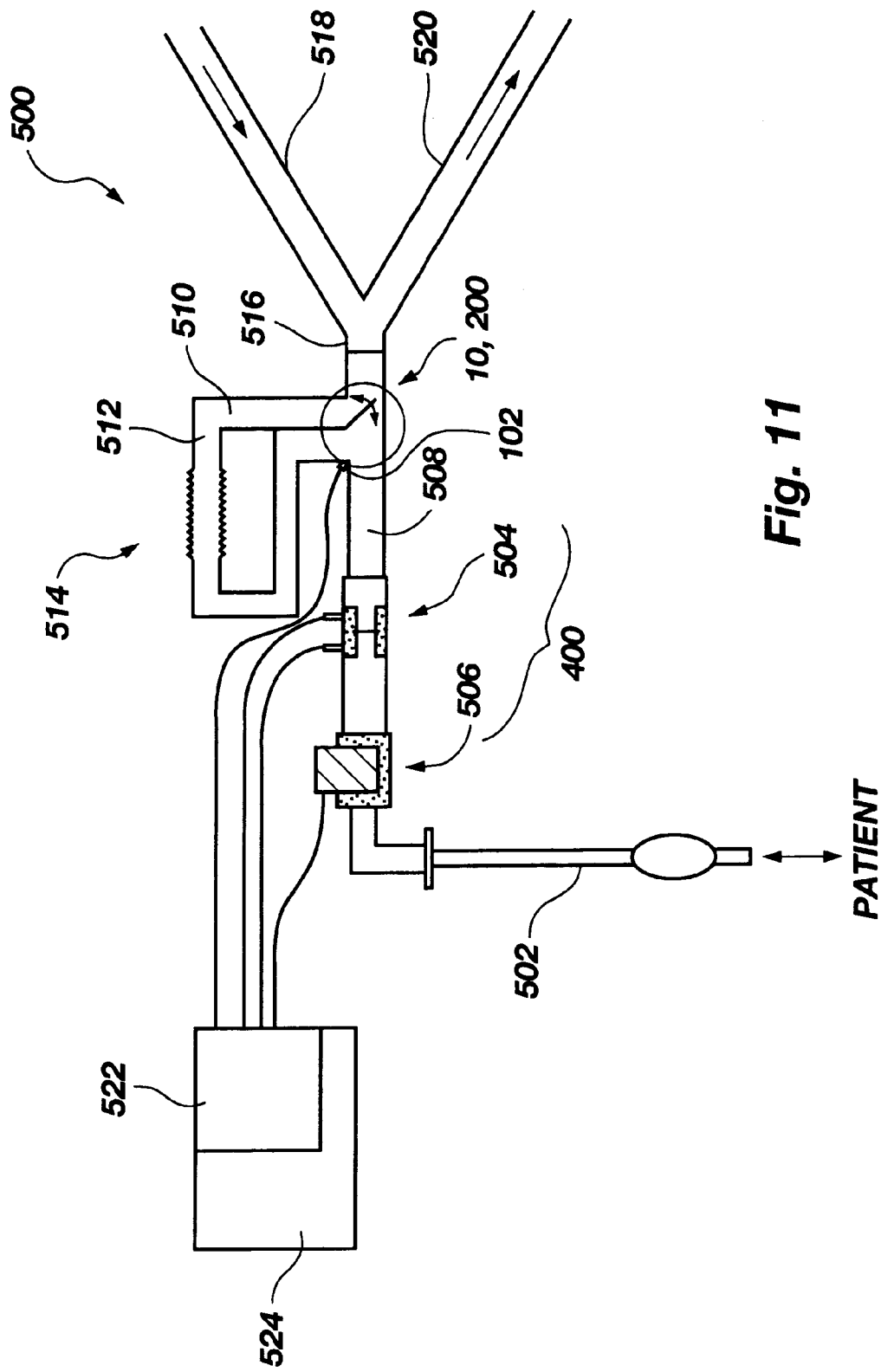
FIG. 11 is a schematic view of a re-breathing system including the airway valve of the invention with associated flow and carbon dioxide sensors and processing equipment, as used with a patient.
Figure 15:
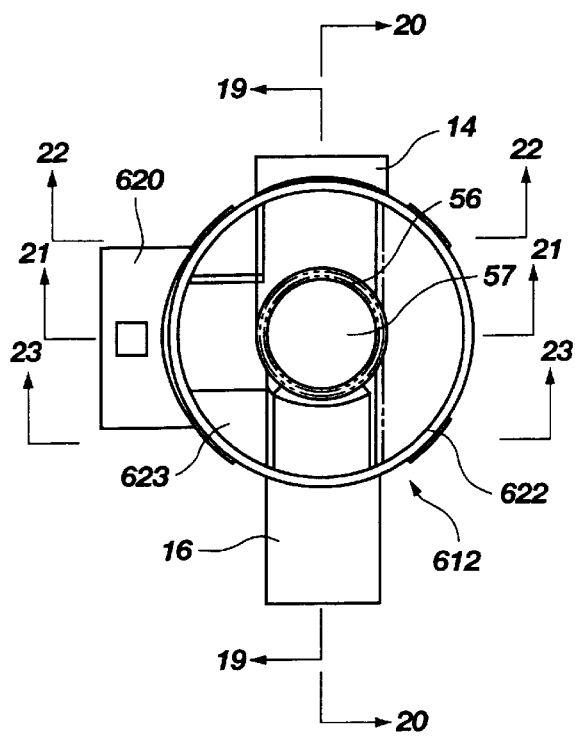
FIG. 15 is a top elevation of the housing for the airway valve embodiment of FIG. 12 with the top cap removed.
Figure 16:
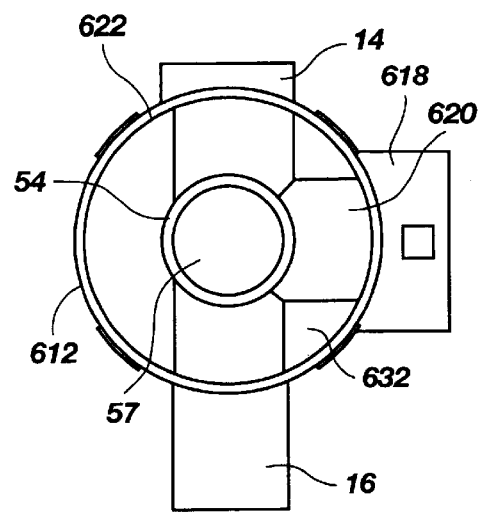
FIG. 16 is a bottom elevation of the housing for the airway valve embodiment of FIG. 12 with the bottom cap removed.
Figure 17:
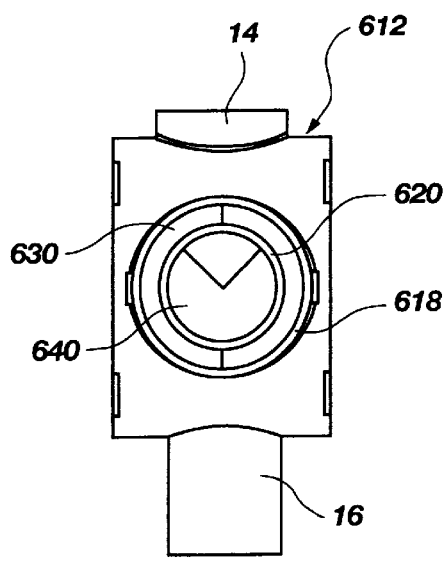
FIG. 17 is a side elevation of the left side of the valve housing of FIG. 15.
Figure 18:
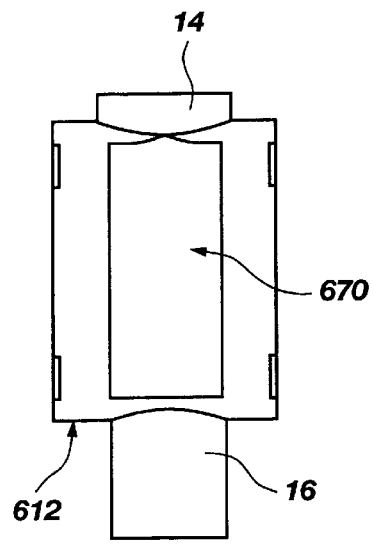
FIG. 18 is a side elevation of the right side of the valve housing of FIG. 15.

Referring now to FIG. 11 of the drawings, a re-breathing equipped ventilator circuit or system 500, which causes a patient to inhale a gas mixture that includes carbon dioxide, is schematically illustrated. Exemplary re-breathing ventilator circuit 500 includes a tubular airway 502 that communicates air flow to and from the lungs of a patient. Tubular airway 502 may be placed in communication with the trachea of the patient by known intubation processes, or by connection to a breathing mask positioned over the nose and/or mouth of the patient, or a mouthpiece for the patient. A flow meter 504, which is typically referred to as a pneumotachometer, and a carbon dioxide sensor 506, which is typically referred to as a capnometer, are disposed between tubular airway 502 and a length of hose 508, and are exposed to any air that flows through ventilator circuit 500. If desired, combined air flow and carbon dioxide sensor 400, as shown in FIG. 2, may be employed in lieu of discrete flow and gas sensors. Both ends of another length or loop of tubing 510, which may be referenced as defining a deadspace or re-breathing volume 512, communicate with hose 508. The two ends of tubing loop 510, and thus deadspace 512, are connected to a two-mode airway valve 10 or 200 according to the present invention, which airway valve 10 or 200 may be operated to selectively direct the flow of air through deadspace 512. Deadspace 512 may optionally include an expandable section 514, which may be provided by the use of corrugated tubing for tubing loop 510. A Y-piece 516, disposed on hose 508 opposite flow meter 504 and carbon dioxide sensor 506, facilitates the connection of an inspiratory hose 518 and an expiratory hose 520 to ventilator circuit 500 and the flow communication of the inspiratory hose 518 and expiratory hose 520 with hose 508. During inhalation, gas flows into inspiratory hose 518 from the atmosphere or a ventilator (not shown). During normal breathing, airway valve 10 or 200 is maintained in the normal operating mode to prevent inhaled and exhaled air from flowing through deadspace 512. During re-breathing, airway valve 10 or 200 is positioned to direct the flow of exhaled and inhaled gases through deadspace 512. Processing unit 522, preferably included within a patient monitor 524, processes air flow and carbon dioxide input signals from sensors 504 and 506, and controls operation of valve 10, 200 to change same from the normal operating mode to the re-breathing mode by initiating and releasing positive air pressure at port 102.

Referring now to FIGS. 12 through 23 of the drawings, yet another embodiment 600 of the airway valve of the present invention will be described. Airway valve 600 is similar in some respects to airway valves 10 and 200, and like components are identified by like reference numerals for clarity. Four tubular elements 14, 16, 618 and 620 extend from plastic housing 612, formed as a truncated cylinder. Tubular elements 14 and 16 are axially aligned and diametrically oriented with respect to housing 612, while tubular elements 618 and 620 are coaxial and extend transversely to elements 14 and 16 and off to one side of housing 612. Coaxial valve body 30 resides within housing 612, and tubular element 14 extending through the wall 622 thereof defines a first primary passage 50 communicating with valve body bore 57 through the wall 52 of valve body 30, at opposing ends of which are located lower valve seat 54 and upper valve seat 56. Discrete tandem diaphragms 24 linked by a shaft 28 are employed (see FIG. 13) as in airway valve 10. Each diaphragm 24 includes a central valve seat contact portion 62 having an enlarged thickness annular seat contact rim 72 at the outer periphery thereof. A thin, annular, flexible skirt portion 74 extends from rim 72 to the outer periphery of each diaphragm 24, at which is located an annular shoulder 276.

Lower diaphragm 24 is clamped to the lower end 634 of housing 612 by bottom cap 232, which is convex, or dome-shaped, and includes an air vent 78 at the center thereof at the bottom of spring retention cavity 306. The mutually cooperative clamping structure of bottom cap 232 and lower end 634 of housing 612 is substantially the same as in valve 200, and so will not be farther described. A coil spring 40 is interposed between bottom cap 232 and lower diaphragm 24, lateral movement of coil spring 40 being prevented by disposition of its lower end in spring retention cavity 306 and its upper end within rim 72.

Upper diaphragm 24 is similarly clamped between top cap 636 and upper end 638 of housing 612, top cap 636 and the upper end 638 of housing 612 being configured substantially the same as bottom cap 232 and lower end 634 of housing 612 for mutual engagement by snap-fit with annular shoulder 276 of upper diaphragm 24 therebetween. Top cap 636 is similar to bottom cap 232, but omits a spring retention cavity and includes a pressure port 102 defined by tubular protrusion 304 at the center of top cap 636.

Tubular element 16 extending through wall 622 of housing 612 defines second primary passage 120, but terminates short of valve body 30, selectively communicating with first primary passage 50 through semi-annular cavity 623 and valve bore 57 when upper valve seat 56 is not occluded by upper diaphragm 24.

Tubular element 618 extending through wall 622 of housing 612 defines first diversion passage 630 with the outer surface of coaxial, smaller tubular element 620, first diversion passage 630 selectively communicating with first primary passage 50 through semi-annular cavity 632 and valve bore 57 when lower valve seat 54 is not occluded by lower diaphragm 24.

Tubular element 620 extends through wall 622 of housing 612 and defines second diversion passage 640, which communicates with second primary passage 120 through semi-annular cavity 623. First diversion passage 630 and second diversion passage 640 communicate exterior to airway valve 600 at the distal end 704 of a coaxial tubing "loop" comprised of an outer tubing segment 700 secured to the outlet of tubular element 618 and a shorter, smaller diameter tubing segment 702 secured to the outlet of tubular element 620. Distal end 704 is closed with a cap 706 sealingly engaged over the end of outer tubing segment 700.

Before proceeding to describe the operation of airway valve 600, the presence of recess 670 in the side of housing wall 622 should be noted, which recess minimizes interior volume within airway valve 600.

In operation, valve 600 is cycled between a normal operating mode and a re-breathing mode by application or release of a positive pressure (i.e., greater than ambient) through pressure port 102. As with airway valves 10 and 200, airway valve 600 is spring-biased to the normal operating mode. In this mode, lower diaphragm 24 is pushed toward lower valve seat 54 by coil spring 40, and communication between first primary passage 50 and first diversion passage 630 is precluded. Upper diaphragm 24, which is linked to lower diaphragm 24 by shaft 28, is pushed upwardly away from upper valve seat 56, permitting communication between first primary passage 50 and second primary passage 120 through semi-annular cavity 623 open annular area 622 and valve bore 57. Upon application of sufficient positive pressure to the closed chamber defined between upper diaphragm 24 and the interior of top cap 636, the force of coil spring 40 is overcome and upper diaphragm 24 is pushed axially downward toward upper valve seat 56 to preclude direct communication within housing 612 between first primary passage 50 and second primary passage 120 in airway valve 600's re-breathing mode. As upper diaphragm 24 is pressed against upper valve seat 56, intermediate shaft 28 transmits the motion of upper diaphragm 24 to lower diaphragm 24, moving same away from lower valve seat 54. Air vent 78 prevents trapping of pressure between lower diaphragm 24 and bottom cap 232, which might otherwise impair operation of airway valve 600. Communication between first primary passage 50 and first diversion passage 630 is thus opened, and an extended airway path (and its attendant increased system volume) is opened between first primary passage 50 and second primary passage 120 through the re-breathing loop or deadspace 512 comprised of the space 708 between coaxial tubing segments 700 and 702 and the bore 710 of inner tubing segment 702, the two communicating at distal end 704. This passage thus interconnects first diversion passage 630 and second diversion passage 640. While second diversion passage 640 is always in communication with second primary passage 120, substantially no air will flow therebetween when lower valve seat 54 is occluded because the path between first diversion passage 630 and first primary passage 50 is closed. It should be noted that airway valve 600 provides its own "tubing loop", defining a deadspace 512, as described above, in lieu of the conventional loop 510, described with respect to FIG. 11, but in other respects, airway valve 600 operates in a similar manner as valves 10 and 200 and may be substituted therefor in the circuit 500 depicted in FIG. 11.

While airway valves 10, 200 and 600 have been described as including interlinked diaphragms which are commonly actuated between modes, the inventors herein contemplate that the present invention includes valves using independently-actuated diaphragms. Specifically, and without limitation, each diaphragm may be individually spring-biased toward a desired position (again, preferably so that the valve defaults to the normal operating mode) and likewise biased by application of a selected positive or negative air pressure (depending on spring position with regard to the diaphragm) to initiate the re-breathing mode of the valve.

While the present invention has been described and illustrated in terms of certain specific embodiments, those of ordinary skill in the art will understand and appreciate that it is not so limited. Additions to, deletions from and modifications to these specific embodiments may be effected without departing from the scope of the invention as defined by the claims. Furthermore, features and elements from one specific embodiment may be likewise applied to another embodiment without departing from the scope of the invention as defined herein.

What is claimed is:

1. An airway valve for diverting respiratory air flow through a secondary path, comprising:

a housing envelope having a wall with first and second primary passages and first and second diversion passages extending therethrough;

a valve assembly within the housing envelope including first and second valve seats at opposing ends of a valve bore in communication with the first primary passage, and first and second diaphragm elements respectively associated with the first and second valve seats;

the second primary passage being communicable within the housing envelope with the first primary passage only through a path closeable by mutual contact of the first diaphragm element and the first valve seat;

the first diversion passage being communicable within the housing envelope with the first primary passage only through a path closeable by mutual contact of the second diaphragm element and the second valve seat; and the second diversion passage being in communication with the second primary passage.

2. The airway valve of claim 1, further including at least one spring element for biasing the first and second diaphragm elements to first positions.

3. The airway valve of claim 2, further including at least one port extending through the housing envelope to an associated closed chamber defined at least in part by one of the diaphragm elements.

4. The airway valve of claim 3, wherein the first and second diaphragm elements are interconnected so as to move in tandem, the at least one spring element being positioned to act on one of the diaphragm elements.

5. The airway valve of claim 4, wherein the first and second diaphragm elements are interconnected by a shaft element extending therebetween.

6. The airway valve of claim 5, wherein the valve bore is linear, the shaft element extends therethrough and each of the diaphragm elements is located outside of the valve bore and adjacent its respective valve seat.

7. The airway valve of claim 6, wherein the housing envelope further includes a housing having a wall through which the first primary passage, the second primary passage, the first diversion passage and the second diversion passage extend, the valve bore is defined by a wall and substantially coaxial with the housing, the first diaphragm element extends across a first end of the housing in sealing engagement therewith, and the second diaphragm element extends across a second end of the housing in sealing engagement therewith.

8. The airway valve of claim 7, wherein the housing further includes a first end cap covering the first end of the housing and the at least one spring element is positioned between the first end cap and the first diaphragm element.

9. The airway valve of claim 8, wherein the first end cap includes a vent aperture therethrough.

10. The airway valve of claim 9, wherein the at least one spring element comprises a coil spring, the first end cap further includes a central, hollow protrusion from an inner surface thereof extending into the coil spring, the vent aperture extends into the protrusion, and the first diaphragm element includes structure engaging at least a portion of a loop of the coil spring.

11. The airway valve of claim 9, wherein the at least one spring element comprises a coil spring, the first end cap further includes a central inwardly-facing recess within which a portion of the coil spring is disposed, the vent aperture extends into the recess, and the first diaphragm element includes structure laterally surrounding at least a portion of the coil spring.

12. The airway valve of claim 8, wherein the housing further includes a second end cap covering the second end of the housing, the at least one port extends through the second end cap and its associated closed chamber is defined between the second end cap and the second diaphragm element.

13. The airway valve of claim 12, wherein the diaphragm elements are maintained in sealing engagement with the housing by engagement of the end caps with their respective ends of the housing.

14. The airway valve of claim 13, wherein the end caps extend over the ends of the housing, and the end caps each include features on an interior surface thereof for engaging features on exterior surfaces of the housing ends over which the end caps extend.

15. The airway valve of claim 14, wherein the end caps each compress a peripheral portion of a diaphragm element against a housing end to effect sealing engagement with the housing.

16. The airway valve of claim 6, wherein the diaphragm elements and the shaft element comprise portions of a unitary structure.

17. The airway valve of claim 6, wherein the diaphragm elements are each formed as separate structures including a portion of the shaft element, the two shaft element portions being engaged to form a complete shaft element.

18. The airway valve of claim 6, wherein the diaphragm elements each comprise a flexible diaphragm having a central aperture therein engaging an end of the shaft element.

19. The airway valve of claim 18, wherein the central aperture extends through each diaphragm element and the shaft element includes increased-diameter tips on ends thereof, each having an adjacent reduced-diameter portion of a length and diameter substantially the same as lengths and diameters of the central apertures of the diaphragm elements, the diaphragm elements residing on the shaft element on the reduced-diameter portions thereof.

20. The airway valve of claim 19, wherein the shaft element further includes a mid-portion of a diameter greater than that of the reduced-diameter portions and including frustoconical portions of increasing diameter toward each of the reduced diameter portions and immediately adjacent thereto, and the tips are of frustoconical configuration of increasing diameter toward the reduced diameter portions and immediately adjacent thereto.

21. The airway valve of claim 7, wherein:

the first primary passage extends diametrically through the housing wall to communicate with the valve bore through an opening through the wall thereof, the second primary passage extends diametrically through the housing wall in alignment with the first primary passage and opens into an open-topped first cavity substantially defined between the housing wall and a wall of the first diversion passage, the valve bore wall and a wall of the first primary passage, said first cavity having a floor extending between the housing wall and the first diversion passage wall, the valve bore wall and the first primary passage wall;

the first diversion passage extends through the housing wall and opens into an open-bottomed second cavity substantially defined between the housing wall and the first diversion passage wall, the valve bore wall and first primary passage wall, said second cavity having a ceiling extending between the housing wall and the first diversion passage wall, the valve bore wall and the first primary passage wall; and the second diversion passage extends through the housing wall and opens into the first cavity.

22. The airway valve of claim 21, wherein the housing comprises a unitary structure.

23. The airway valve of claim 22, wherein the first and second diversion passages are located on opposite sides of the second primary passage.

24. The airway valve of claim 23, wherein the first and second diversion passages are oriented at about 30° angles to the second primary passage.

25. The airway valve of claim 7, wherein:

the first primary passage extends diametrically through the housing wall to communicate with the valve bore through an opening through the wall thereof, the second primary passage extends diametrically through the housing wall in alignment with the first primary passage and opens into an open-topped first cavity substantially defined between the housing wall and the valve bore wall, a first vertically extending wall between the housing wall and the valve bore wall and a second vertically extending wall between the housing wall and the valve bore wall, the first cavity having a floor extending between the housing wall, the valve bore wall and the first and second vertically extending walls;

the first diversion passage extends through the housing wall and opens into an open-bottomed second cavity including a first portion substantially defined between the housing wall, a wall of the first primary passage and a third vertically extending wall between the housing wall and the valve bore wall, the second cavity first portion having a first ceiling portion extending between the housing wall, the first primary passage wall and the third vertically extending wall, the second cavity including a second portion defined between the housing wall and the first primary passage wall, the valve bore wall and the second vertically extending wall, the second cavity second portion having a second ceiling portion extending between the housing wall and the first primary passage wall, the valve bore wall and the second vertically extending wall; and the second diversion passage extends through the housing wall and opens into the first cavity.

26. The airway valve of claim 25, wherein the housing comprises a unitary molded structure.

27. The airway valve of claim 26, wherein the first and second diversion passages are located on a common side of the housing and substantially transverse to the first and second primary passages.

28. The airway valve of claim 27, wherein the first and second diversion passages are mutually parallel.

29. A method of operating an airway valve for diverting respiratory air flow between a primary path within a housing of the airway valve and an alternative path exterior thereto, comprising:

opening communication within the housing between a first primary passage and a second primary passage by positioning a first diaphragm element away from a first valve seat while simultaneously closing communication between the first primary passage and a first diversion passage by positioning a second diaphragm element in contact with a second valve seat responsive to force provided by a single spring element; and closing communication within the housing between the first primary passage and the second primary passage by positioning the first diaphragm element in contact with the first valve seat while simultaneously opening communication between the first primary passage and a second diversion passage by positioning the second diaphragm element away from the second valve seat responsive to force provided by an air pressure differential applied to the first diaphragm element and sufficient to overcome the single spring element force.

30. The method of claim 29, further comprising transmitting forces between the first and second diaphragm elements with a shaft element passing through a valve bore extending between the first and second valve seats.

* * * * *